(12) United States Patent
Dittmann et al.

(10) Patent No.: US 8,143,223 B2
(45) Date of Patent: Mar. 27, 2012

(54) CYTOPROTECTION BY MEANS OF PHOSPHOTYROSINE

(75) Inventors: Klaus Dittmann, Tuebingen (DE); Claus Mayer, Tuebingen (DE); Peter Rodemann, Stuttgart (DE)

(73) Assignee: Eberhard-Karls-Universitaet Tuebingen Universitaetsklinikum, Tuebingen (DE)

( * ) Notice: Subject to any disclaimer, the term of this patent is extended or adjusted under 35 U.S.C. 154(b) by 1158 days.

(21) Appl. No.: 10/677,818

(22) Filed: Oct. 2, 2003

(65) Prior Publication Data

US 2004/0142908 A1 Jul. 22, 2004

Related U.S. Application Data

(63) Continuation of application No. PCT/EP02/03403, filed on Mar. 27, 2002.

(30) Foreign Application Priority Data

Apr. 3, 2001 (DE) .................................. 101 17 834

(51) Int. Cl.
*A61K 35/00* (2006.01)
(52) U.S. Cl. ........................................ 514/19.3; 514/7.5
(58) Field of Classification Search ............. 514/114, 514/7.5, 19.3
See application file for complete search history.

(56) References Cited

U.S. PATENT DOCUMENTS 6,534,056 B1 * 3/2003 Tromblay et al. .......... 424/146.1

FOREIGN PATENT DOCUMENTS

EP 0 728 469 A2 8/1996
EP 0728469 A2 * 8/1996

OTHER PUBLICATIONS

Ramsay et al., "Ultraviolet-B Phototherapy for Early-Stage Cutaneous T-Cell Lymphoma", Jul. 1992, vol. 128 No. 7, abstract.*
"Definitions, Conversions, and Claculations for Occupational Safety and Health Professionals", 2006, CRC Press, Third Edition, pp. 8-3 to 8-7.*
Mishra et al., "O-Phospho-L-tyrosine Inhibits Cellular Growth by Activating Protein Tyrosine Phosphatases", Feb. 11, 1993, Cancer Research, vol. 53, pp. 557-563. (See IDS submission).*
Blomqvist et al., "The combination of radiotherapy, adjuvant chemotherapy (cyclophosphamide-doxorubicin-ftorafur) and tamoxifen in stage II breast cancer. Long term follow-up results of a randomized trial", 1992, British Journal of Cancer, vol. 66, pp. 1171-1176.*
Dittman K.H. et al. "O-phospho-L-tyrosine protects TP53 wild-type cells against ionizing radiation," International Journal of Cancer, 96 (2001) pp. 1-6.
Mishra, Shrikant et al. "Association of inhibition of cell growth by O-phospho-L-tyrosine with decreased tyrosine phosphorylation", Cancer Letters, 102 (1996) pp. 65-71.
Mishra Shrikant et al. "O-Phospho-L-tyrosine inhibits cellular growth by activating protein tyrosine phosphatases," Cancer Research, 53 (1993) pp. 557-563.

* cited by examiner

*Primary Examiner* — Karlheinz R Skowronek
*Assistant Examiner* — Ali Soroush
(74) *Attorney, Agent, or Firm* — Knobbe Martens Olson & Bear LLP

(57) ABSTRACT

The present invention relates to a method for protecting biological material from cell damaging factors, a method for producing a pharmaceutical composition for the prophylactic and/or therapy accompanying treatment of radiation therapy patients and/or chemotherapy patients, a cosmetic composition, and a culture medium.

7 Claims, 6 Drawing Sheets

CYTOPROTECTION BY MEANS OF PHOSPHOTYROSINE

RELATED APPLICATIONS

This application is a continuation of co-pending international application PCT/EP02/03403 filed on Mar. 27, 2002 and designating the U.S., which was published in German, and claims priority of German patent application DE 101 17 834.4 filed on Apr. 3, 2001, which is incorporated herein by reference.

BACKGROUND OF THE INVENTION

1. Field of the Invention

The present invention is concerned with protecting biological material from cell-damaging factors.

2. Description of the Related Art

It is known that the integrity of biological material, such as animal or human cells, tissues or organisms, can be damaged by a large number of a very wide variety of factors. These factors, can, for example, be energy-rich or ionizing radiation, such as radioactive radiation, X-radiation, cosmic radiation, etc., or ultraviolet light (UV light). While ionizing radiation is on the one hand one of the noxious environmental factors, on the other hand it can also be employed usefully in medicine. In this connection mention may be made of X-ray diagnostics, nuclear medicine and radiation therapy. This energy-rich radiation is characterized by the fact that it has the ability to ionize molecules.

Other important cell-damaging factors are chemical agents, for example, in the form of environmental poisons, but also such chemical agents which are used in the context of medical treatments as therapeutic agents, for example cytostatic agents. The latter are a chemically heterogeneous group of cytotoxic pharmacological substances which prevent, or delay substantially, the division of functionally active cells by affecting their metabolism in a variety of ways. Cytostatic agents are principally used in tumor therapy, with the starting-point for their activity being the fact that the rate at which tumor cells divide is higher than that of normal cells. Various groups of cytostatic agents are known: alkylating agents (e.g., cisplatin); antimetabolites (e.g., folic acid antagonists); mitosis inhibitors, antibiotics (e.g., bleomycin); enzymes (e.g., L-asparaginase); and others.

These factors can induce damage at all levels of biological organization, thus, reactions at the molecular or macromolecular (e.g., nucleic acid) level and at the cellular level, or tissue reactions or reactions involving the entire organism are seen in response to the influence of these factors.

Examples of damage which is induced by energy-rich radiation or ultraviolet radiation are an alteration of DNA, that is mutagenesis, which can lead to tumor development, and the degeneration, atrophy, fibrosing or necrosis of such tissues which are subjected to a high level of radiation.

Thus, the development of malignant melanoma, for example, is promoted by the skin being exposed extensively to the sun.

As was mentioned at the outset, the human organism is confronted with particularly high radiation intensities not only in connection with a high level of exposure to sunlight, but also during X-ray diagnosis, when there is an appropriate medical indication, or when radiation therapy is used in connection with tumor diseases. Radiologists, dentists, traumatologists, technical assistants in radiology, and workers in X-ray tube factories, are also particularly at risk in this connection.

The abovementioned cytostatic agents, which are to be categorized as being particularly important as far as causing cell damage is concerned, cause damages when used in the human body especially because the differences in division rate between normal and tumor cells are insufficient for selectively targeting tumors in a specific manner. The undesirable side effects or cytostatic agents therefore result, in particular, from a general inhibition of the regeneration of rapidly proliferating tissue. Blood cell formation, epithelia of the mucous membranes, whose inhibition of regeneration leads to gastrointestinal disturbances, and skin and skin appendages, whose inhibition of regeneration leads to hair loss, are particularly affected.

SUMMARY OF THE INVENTION

Against this background, an object of the present invention is to provide a protection of biological material from cell-damaging factors.

According to the invention, this object is achieved by using phosphotyrosine for the said purposes.

Phosphotyrosine (also termed P-Tyr below) is a modified amino acid which is derived from the aromatic amino acid tyrosine and in which the hydroxyl group of the phenyl of the side chain has been phosphorylated. Phosphotyrosine is described in a large number of biochemistry, molecular biology and protein chemistry textbooks.

The inventors have surprisingly found that this phosphorylated amino acid protects biological material from cell-damaging factors.

In this connection, within the meaning of the invention, phosphotyrosine is understood as being O-phospho-L-tyrosine (L-3-[4-hydroxyphenyl]alanine-4'-phosphate), as well as O-phospho-D-tyrosine (D-3-[4-hydroxyphenyl]alanine-4'-phosphate) and O-phospho-DL-tyrosine (DL-3-[4-hydroxyphenyl]alanine-4'-phospate).

In this connection, biological material is to be understood as being any biological, structured unit such as a cell (in culture or in a tissue formation), tissues, organs, organisms, etc.

Within the meaning of the invention, cell-damaging factors are to be understood as being influences which have a negative effect on the integrity and/or viability of biological material, such as ionizing radiation (radioactive radiation, X-radiation, cosmic radiation, etc.), ultraviolet light and chemicals of any type, in particular cytostatic agents (for example alkylating compounds such as cisplatin).

By the use of phosphotyrosine is to be understood that this modified amino acid is either brought into contact, in a suitable, for example, galenic preparation, with biological material, for example, applied to an organism or introduced into this organism, or brought into contact, in some form in vitro, with biological material, e.g., isolated cells, tissues or organs. In this connection, the bringing-into-contact with the phosphotyrosine can take place before, during or after the exposure to cell-damaging factors.

Within the meaning of the invention, protection of biological material means that the damage induced by said cell-damaging factors is reduced or prevented by phosphotyrosine.

An advantage of the use of phosphotyrosine according to the invention is to be seen in the fact that phosphotyrosine can be prepared or obtained cost-saving in large quantities. No peptide synthesis or elaborate protein purification is required for this purpose.

In addition, phosphotyrosine is markedly more resistant to degradation than are peptides or proteins. As a result, a galenic preparation is also substantially more simple and more stable.

Due to the small molecular size of the phosphotyrosine its possible uptake into the cells to be treated is facilitated, with this resulting in good cytoprotective activity.

In addition, because of its small size, there is not expected to be any danger of immunological reactions when phosphotyrosine is introduced into or applied onto an organism.

The cytoprotective properties of phosphotyrosine are also surprising because so far completely different activities have been ascribed to it. Thus, for example, Shrikant Mishra and Anne W. Hamburger have shown that phosphotyrosine inhibits the growth of human breast and kidney carcinoma cells ("O-phospho-L-tyrosine inhibits cellular growth by activating protein tyrosine phosphatases", Cancer Research 53, pp. 557-563, 1993) and that this growth inhibition is effected in a P-Tyr dose-dependent manner ("Exogenous phosphotyrosine modulates epidermal growth factor receptor tyrosine phosphorylation", Carcinogenesis 14, pp. 269-273, 1993). This research group demonstrated in the case of two other tumor cell lines, i.e. a liver carcinoma cell line and arc-transformed NIH 3T3 cells, the ability of phosphotyrosine to inhibit cell growth ("Association of inhibition of all growth by O-phospho-L-tyrosine with decreased phosphorylation", Cancer Letters 102, pp. 65-71, 1996).

The inventors of the present invention were unable to confirm this inhibitory effect of exclusively administering phosphotyrosine on tumor cell growth. On the other hand, they were surprisingly able to observe that, after irradiation with ionizing rays, there is a higher rate of death in tumor cells which have been pretreated with phosphotyrosine than in tumor cells which have not been pretreated.

It furthermore emerged that, in contrast to the situation in tumor cells, normal cells which have been pretreated with phosphotyrosine exhibit a significantly higher survival rate than do normal cells which have not been pretreated with phosphotyrosine both after irradiation with ionizing rays and after treatment with cisplatin.

This selectivity of the cytoprotective property of phosphotyrosine for normal cells, that is for healthy, non-tumor cells, was not to be expected in the light of the properties of phosphotyrosine which were known in the prior art and which were described in a completely different connection.

This object underlying the invention is thus achieved completely.

In a preferred embodiment, the phosphotyrosine is used for protecting biological material from radiation, preferably ionizing radiation and/or ultraviolet light.

This has the particular advantage that thereby a use is provided which offers protection from particularly important cell-damaging factors to which virtually every human organism is also at least partially exposed.

Furthermore it is preferred to use phosphotyrosine for protecting biological material against chemicals, preferably cytostatic agents.

As mentioned at the outset, chemicals, in particular cytostatic agents, play an important role as cell-damaging factors.

This preferred use of phosphotyrosine according to the invention consequently provides effective protection against particularly important cell-damaging factors.

In a preferred further development, phosphotyrosine is used for protecting the skin.

This has the particular advantage that thereby an organ is protected which is constantly exposed to cell-damaging factors of a physical or chemical nature, for example in the form of solar radiation or in the form of environmental poisons.

In this connection, it is also advantageous that phosphotyrosine is stable under oxidizing conditions, that is, for example, in air, and can exert a long-lasting protective effect, e.g., against the UV rays of the sun. Phosphotyrosine is therefore suitable for being used for protecting the skin against a high level of solar irradiation. The use of phosphotyrosine for this purpose has the further advantage that, because of its small size, phosphotyrosine can penetrate into the skin and persists in this location for a long period.

Furthermore it is preferred to use phosphotyrosine within the context of a radiation therapy for tumor patients.

In such a radiation therapy, ionizing radiation is used, for example, for treating malignant neoplasias. The aim in this connection is to damage the tumor tissue to the greatest possible extent while at the same time sparing the surrounding healthy tissue. Because of its previously mentioned properties, as identified by the inventors, the use of phosphotyrosine in this connection has the particular advantage that it selectively protects healthy, that is normal, tissue from cell damage but does not, on the other hand, display any cytoprotective properties for tumor tissue and, on the contrary, even promotes the death of such tissue.

Furthermore, it is preferred to use phosphotyrosine within the context of a chemotherapy for tumor patients.

In chemotherapy, chemotherapeutic agents or cytostatic agents are used specifically for inhibiting the growth of tumor cells in the body, with the aim being to protect healthy cells from the cytotoxic activities of the chemotherapeutic agents. Because of its properties which have been identified and described above, the use of phosphotyrosine according to the invention consequently has the particular advantage of providing a cytoprotector which is selective for healthy cells.

An object of the present invention is also the use of phosphotyrosine for producing a pharmaceutical composition for the prophylactic and/or therapy-accompanying treatment of radiation therapy patients and/or chemotherapy patients.

For this, the phosphotyrosine can be prepared in the galenicals which are in each case appropriate and usual, i.e. be present, where appropriate, together with usual carrier substances, auxiliary substances and/or additives. A pharmaceutical composition of this nature can be administered intravenously, example percutaneously, by means of a local injection, for into the regions or cavities of the body which are directly affected by the cell-damaging factor, or else by means of being applied locally.

Such a use for producing a pharmaceutical composition additionally has the advantage that, as the active substance in this composition, the modified amino acid in question can express its cytoprotective effect without at the same time eliciting any dangerous immune reactions. Thus, because of its small size, phosphotyrosine only has low immunogenicity, which means that no allergic reaction is to be expected when the pharmaceutical composition is used on or in the human or animal body, and that antibodies are not involved in eliminating the phosphotyrosine from the given organism in this connection.

The cytoprotective activity of phosphotyrosine, which activity is selective for healthy, normal cells, and its toxicity-promoting property, which is selective for tumor cells in connection with irradiation, makes the use of this compound particularly suitable for producing a pharmaceutical composition.

Another object of the invention is a cosmetic composition which comprises phosphotyrosine and, where appropriate, other usual carrier substances, auxiliary substances and/or additives.

Such a cosmetic composition can be administered, for example, as a sunscreen milk, skin cream or the like. It then comprises the usual constituents of such compositions (such as oils, emulsions, pigments, etc.). The cosmetic composition can, of course, additionally comprise UV filters such as, derivatives of p-amino benzoic acid, salicylic acid, cinnamic acid, dibenzoylmethane or the like.

As a result of the cytoprotective activity of the phosphotyrosine, such a cosmetic composition provides ideal protection, especially against the UV radiation in sunlight. Since, because of its small size, the phosphotyrosine can even penetrate into the skin, and is, furthermore, stable over a long period, it is possible, in this way, to achieve long-term protection against radiation. In this connection, it is also necessary to consider creams which can provide effective skin protection, for example by the cream being worked into the hands, for individuals who have a high level of involvement with toxic chemicals.

Object of the present invention is also a culture medium which contains phosphotyrosine and, where appropriate, other usual buffering substances, carrier substances, auxiliary substances and/or additives.

It has emerged that, when being transported, with this transport frequently taking place using aircraft at a great height, cells in culture, or else organs, lose 50% or more of their viability as a result, for example, of being stressed by cosmic radiation. Apart from providing suitable conditions for storage and cultivation, the culture medium according to the invention also provides the biological material which is present in the culture with an effective protection against cell-damaging factors, e.g., radiation, as a result of the cytoprotective properties of the phosphotyrosine. This thereby ensures that cell samples or organs even withstand long routes of transport, for example by using aircraft, with little or no loss of viability.

In the culture medium according to the invention it is preferred to use phosphotyrosine in a concentration range of from 1 to 100 μM. Thus, investigations carried out by the inventors have shown that the cytoprotective effect of the phosphotyrosine is particularly high in this range. This finding is especially surprising because the abovementioned experiments performed by Mishra and Hamburger were carried out at P-Tyr-concentrations of 1.67 mM, with some even being carried out at 16.7 mM, even if these experiments demonstrated a different effect of the phosphotyrosine.

It will be understood that the features mentioned above, and those which are still to be explained, can be used not only in the combinations which are in each case indicated but also in other combinations, or on their own, without departing from the scope of the present invention.

BRIEF DESCRIPTION OF THE DRAWINGS

Further advantages are evident from the following embodiments and in connection with the drawings, in which.

DETAILED DESCRIPTION OF THE PREFERRED EMBODIMENT

Example 1

Figure 1:
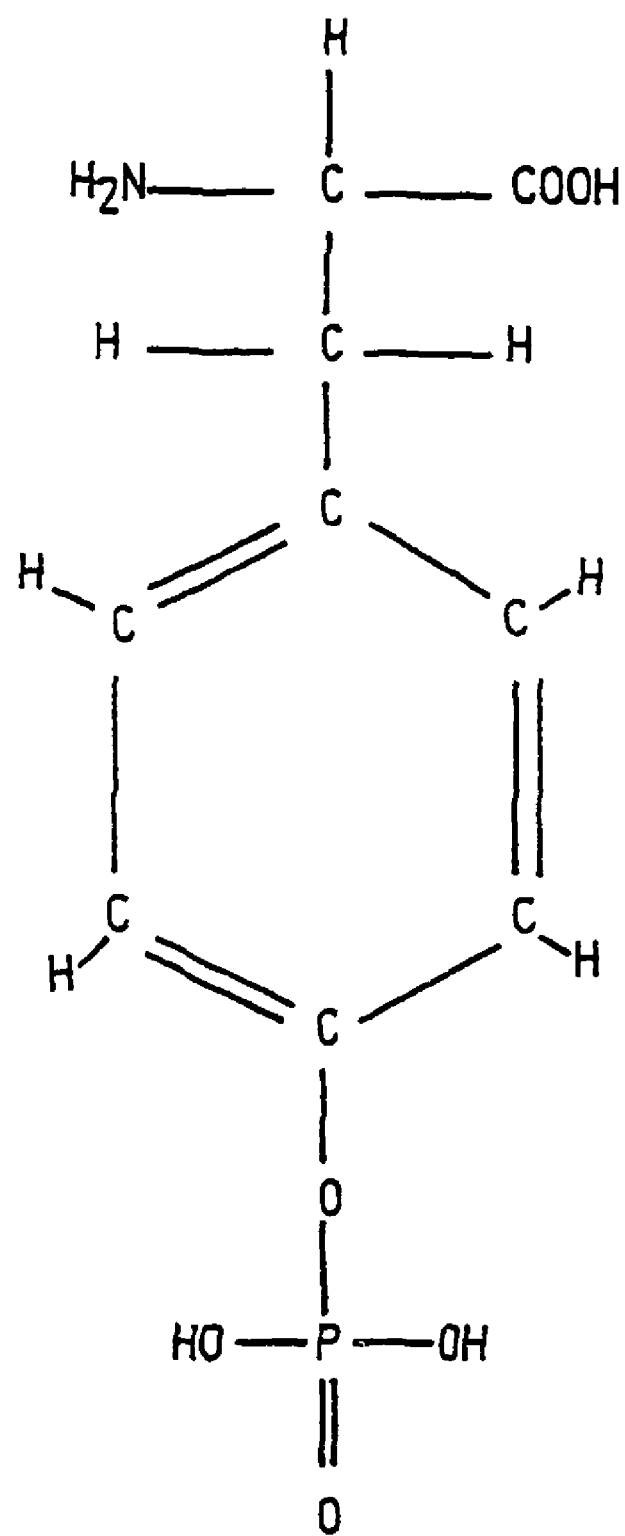
FIG. 1 shows the chemical structural formula of phosphotyrosine (P-Tyr) or O-phospho-L-tyrosine (L-3-[4-hydroxyphenyl]alanine-4'-phosphate) in ionized form.

Cell Cultures Used for Investigating the Cytoprotective Effect of Phosphotyrosine Human fibroblasts (cell strains HSF1 and HSF6, which are derived from human skin, passages 9 to 15; CCD32, which is derived from embryonic lung tissue, passages 9 to 11) are particularly well suited for investigating the cytoprotective properties of the phosphotyrosine.

In addition, it is possible to use the human squamous carcinoma cell lines HTB-35 (ATCC, which is derived from a cervical carcinoma, passage unknown, used in passage 10 after receipt) (Srivastava et al., "The status of the p53 gene in human papilloma virus positive or negative cervical carcinoma cell lines", Carcinogenesis 13, pages 1273-1275, 1992) and HTB-43 (ATCC, is derived from a hypopharyngeal tumor, passage 124). Both carcinoma cell lines are characterized by a point mutation in the p53 gene (Kim et al., "State of p53, Rb and DCC tumor suppressor genes in human oral cancer cell lines", Anticancer Research, pages 1405-1413, 1993).

Transformed human fibroblasts, e.g., the cell line HH4dd (is derived from human skin, passages 65 to 70), are also suitable for the investigation. This cell line is derived from the normal cell strain HH4 and is likewise characterized by a p53 mutation (Dittmann et al., "The radioprotective effect of BBI is associated with the activation of DNA-repair relevant genes", Int. J. Radiat. Biol. 74, pages 225-230, 1998). HH4dd grows in soft agar, is characterized by its aneuploidy and induces tumors in nude mice.

The cells are cultured in Dulbecco's modified Eagle's medium (DMEM) supplemented with 10% fetal calf serum (FCS) (GIBCO/BRL, Eggenstein, Germany, article No. 40G7285K) (=normal medium), under standard conditions.

Example 2

Irradiating Cells, Incubating with Cisplatin

The cells, which have grown to confluence, are incubated for 16 hours either in simple normal medium or in medium which contains phosphotyrosine, phosphoserine or phosphothreonine (Sigma, Munich, Germany) at the given concentrations.

For the radioactive irradiation, the cells are irradiated with 4 MV photons using a "Linac" (Mevatron$^{60}$/Siemens, Erlangen, Germany) using a dose rate of 2 Gy/min at room temperature, as described (Dittmann et al. "Bowman-Birk Proteinase inhibitor modulates radiosensitivity and radiation-induced differentiation of human fibroblasts in culture", Radiother. Oncol. 34, pages 137-143, 1995).

The cells are irradiated with UV light (312 nm) at a dose rate of 450 J/m$^2$ per minute using a UVB lamp (Bioblock Scientific, Illkirch Cedex, France).

The incubation with cisplatin take place at a concentration of 1 μg of cisplatin/ml (cis-diammine platinum(II-dichloride); Sigma, Munich, Germany).

Example 3

Clonogenic Assay (=Colony-Forming Assay)

The investigations concerning the cytoprotective property of phosphotyrosine is performed via the so-called clonogenic assay, which is described, for example, by Dittmann et al., 1995, loc. cit., and which is briefly explained below.

The cells, which are cultured as described in Example 1 and which are either incubated with the cell-damaging factors as described in Example 2 or remain untreated as controls, are freed from medium, washed and detached from the substrate using 0.05% trypsin and 0.1% EDTA. For the purpose of analyzing colony formation, the detached cells are plated at a constant cell density of 1500 cells per 78 cm$^2$ dish. The plated cells were then incubated for 14 days in normal medium additionally containing 20% FCS. This period of time enabled colony formation to take place.

In this connection, a colony is a mass of cells which develops, during the 14 days of culture, from a single cell as a result of consecutive cell divisions. This colony is also termed a clone. In the sense of clonogenic survival, the number of colonies or clones corresponds to the extent of the damaging effect of a chemical or physical agent. If many cells die during the treatment with the cell-damaging factors, only a few colonies are then formed after 14 days; if many cells survive, many colonies can then be counted after the 14 days of culture. Consequently, the clonogenic survival of the cells after a cell-damaging treatment is a direct measure of the cytoprotective effect of the phosphotyrosine.

After the 14 days of culture, the cells are fixed, stained and counted as described (Dittmann et al., 1995, loc. cit.). When determining clonogenic survival, the colonies containing more than 50 cells are counted per plate. The counting take place after the culture dishes have been coded and is carried out by two individuals independently of each other.

The result of such a clonogenic assay is expressed as "relative cytoprotection" or in "% number of the clones", with the number of the colonies formed in the different assays being related to each other.

Example 4

Figure 2:
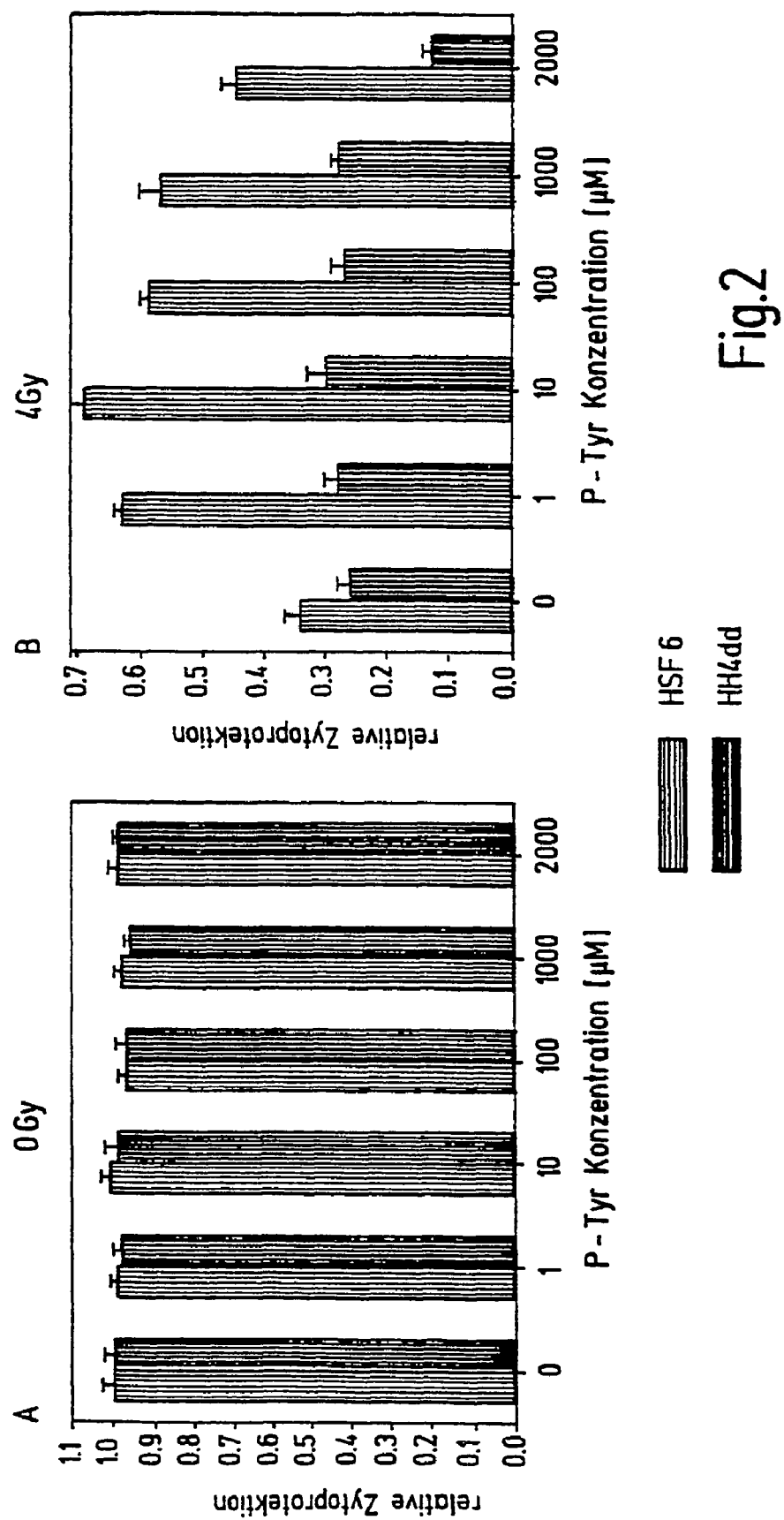
FIG. 2 shows the survival of normal skin fibroblasts, as compared with transformed fibroblasts, after pretreatment with different P-Tyr-concentrations and after radioactive irradiation.

Reaction of the Fibroblasts to Radioactive Irradiation after Having been Pretreated with Different Doses of Phosphotyrosine Normal skin fibroblasts (HSF6) were incubated for 16 hours with P-Tyr, whose chemical structural formula is shown in FIG. 1, in a concentration range of from 0 to 2000 μM. The clonogenic survival was then determined, as described under Example 3, without any cell-damaging treatment. The result of such an experiment is shown in FIG. 2A.

In this figure, the pale grey bars indicate the fraction of the HSF6 cells which survived while the dark grey bars indicate the fraction of the HH4dd cells which survived. As the figure shows, pretreating with P-Tyr alone at concentrations of up to 2000 μM does not have any effect on the clonogenic survival of the HSF6 cells. Comparable results were obtained for the transformed fibroblast cell line HH4dd. In this case, too, and unexpectedly in view of the results of Mishra and Hamburger (loc. cit.), no effect was seen on clonogenic survival (FIG. 2A).

On the other hand, the combined treatment with phosphotyrosine and ionizing irradiation, at an energy dose of 4 Gy, demonstrated a clear increase in clonogenic survival in the case of normal fibroblasts. Maximum survival was achieved at a P-Tyr concentration of 10 μM (FIG. 2B; pale grey bars). However, with the same treatment, and under the same exposure conditions, no increase in clonogenic survival was observed in the case of the transformed HH4dd fibroblasts. On the contrary, the treatment of the transformed fibroblasts with 2000 pM P-Tyr resulted in a significant increase in the toxicity of the radiation; see FIG. 2B.

Example 5

Comparison of the Radioprotective Effect of Phosphotyrosine with that of Phosphoserine and Phosphothreonine In order to test whether other phosphorylated amino acids, such as phosphoserine (P-Ser) or phosphothreonine (P-Thr), also exhibit radioprotective effects which are comparable with those of P-Tyr, untransformed fibroblasts (HSF1) were pretreated for 16 hours with equimolar concentrations of these two amino acids (in each case 10 μM) and then subjected to an ionizing irradiation with 4 Gy as described under Example 2; the results of a clonogenic assay were then compared with those for P-Tyr.

Figure 3:
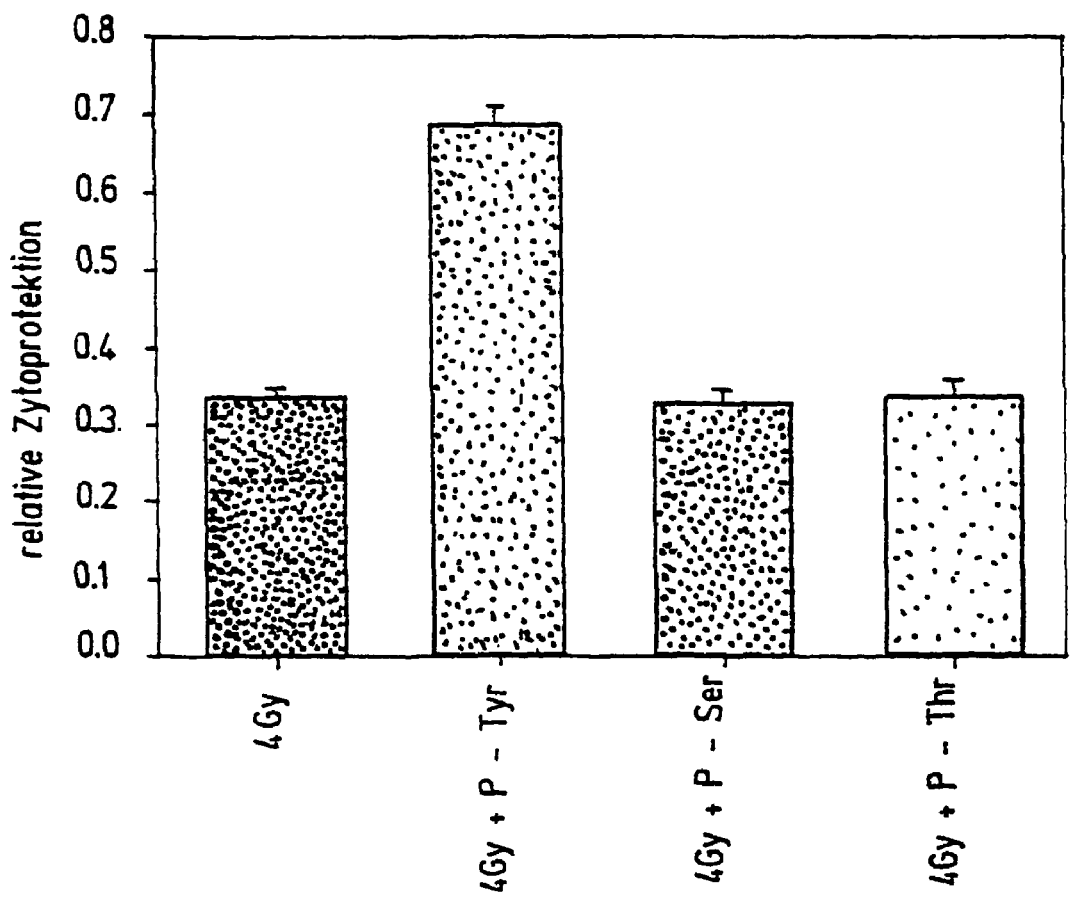
FIG. 3 shows a comparison of the radioprotective effect or phosphotyrosine, phosphoserine and phosphothreonine on normal fibroblasts.

The result of such an experiment is shown in FIG. 3. It is found that, while preincubating normal fibroblasts with P-Tyr resulted in significant radioprotection (2nd bar from the left), incubating with P-Ser or P-Thr under identical experimental conditions did not result in any radioprotection (3rd and 4th bars from the left).

Example 6

Figure 4:
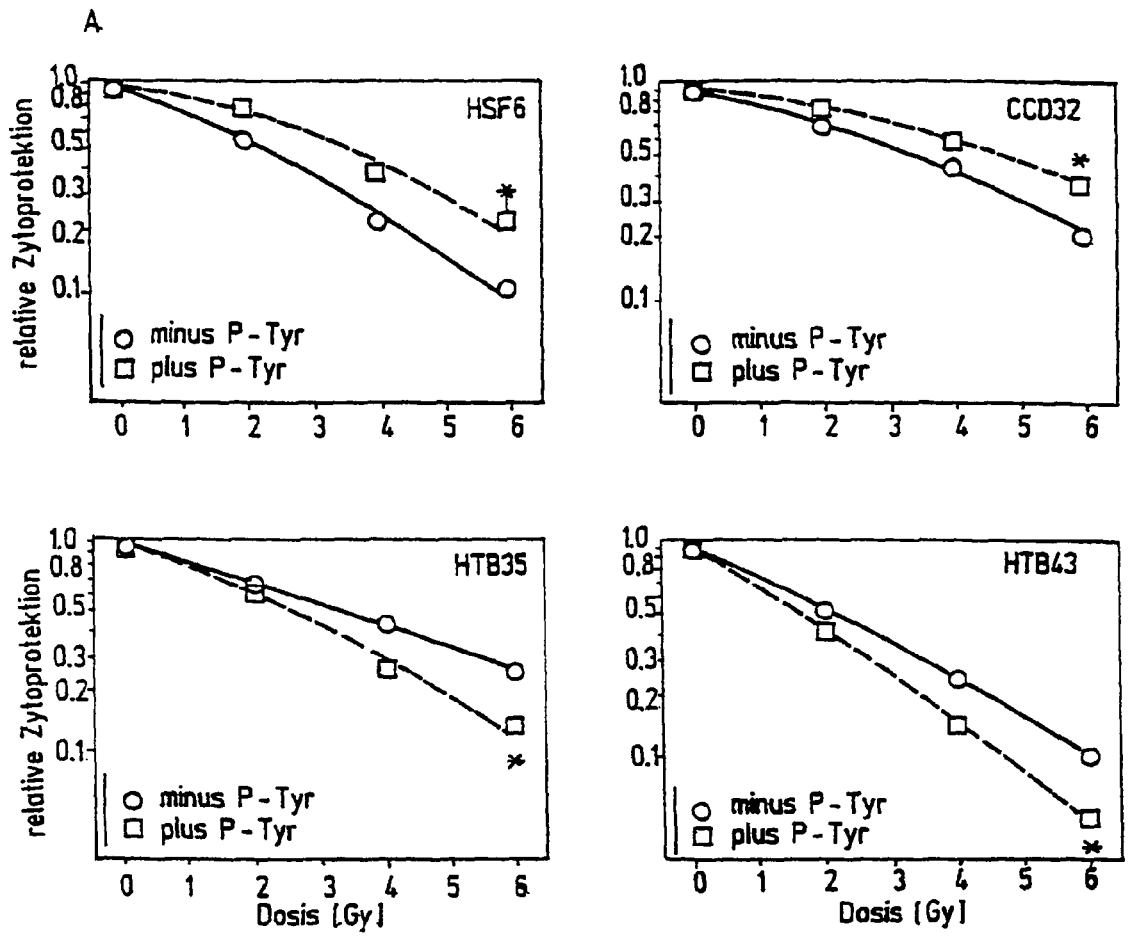
FIG. 4 shows the radioprotective effect of a preincubation with P-Tyr on healthy non-tumor cells as compared with tumor cells.

Reaction of Fibroblasts to Different Doses of Ionizing Irradiation after Pretreatment with Phosphotyrosine The cell strains HSF6 and CCD32, and the cell lines HTB-35 and HTB-43, were preincubated for 16 hours with 10 μM P-Tyr. The cells were then irradiated with doses of from 0 to 6 Gy and the clonogenic survival was determined after a period of 6 hours. Each data point in such an experiment, shown in FIG. 4A, represents the mean value of several measurements and the standard deviation. The curve fit was calculated here using the linear quadratic model and α and β values were determined and tested for significance using the Student t-test. The asterisks indicate a significance difference ($p<0.05$) for α or β or both. FIG. 4B shows, in tabular form, the mean value of the relative cytoprotection from the four measured values (SF4) for each assay and the standard deviation, including the p-value.

Pretreatment of normal skin fibroblasts (HSF6) and normal lung fibroblasts (CCD32) with 10 μM P-Tyr lead to a significant increase in clonogenic survival up to a dose of 6 Gy (FIG. 4A, upper row, FIG. 4B, rows 1 and 2). On the other hand, pretreating the transformed cell lines (HTB-35 and HTB-43) with P-Tyr resulted in a significant reduction in clonogenic survival (FIG. 4A, lower row, FIG. 4B, rows 3 and 4).

These results show that, while a pretreatment of healthy, that is normal, cells with phosphotyrosine efficiently protects these cells from cell-damaging factors, a pretreatment of tumor cells with phosphotyrosine leads to an increase in the death of these transformed cells when they are incubated with cell-damaging factors.

Example 7

Reaction of Phosphotyrosine-Pretreated Fibroblasts to UVB Irradiation

In order to test the cytoprotective protection of phosphotyrosine in regard to non-ionizing radiation, normal, untransformed, fibroblasts (HSF1) and transformed fibroblasts (HH4dd) were pretreated with 10 µM P-Tyr for 16 hours and then irradiated with 200 J of UVB; they are then investigated 7 hours later in a clonogenic assay as described in Example 3.

Figure 5:
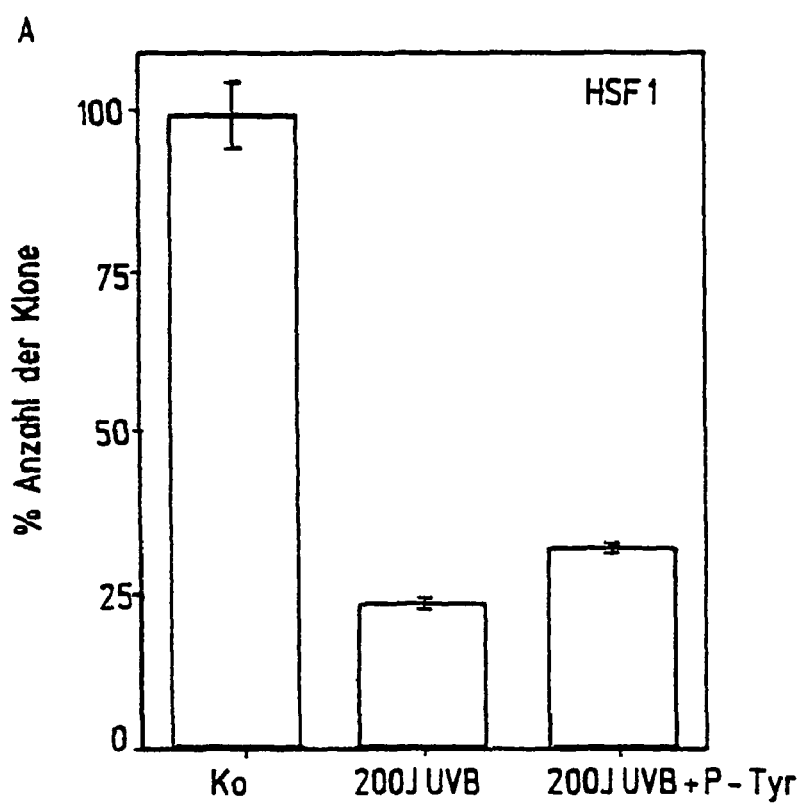
FIG. 5 shows the clonogenic survival of normal fibroblasts after irradiation with UVB, in dependence on a pretreatment with P-Tyr, as compared with tumor cells.
Figure 5:
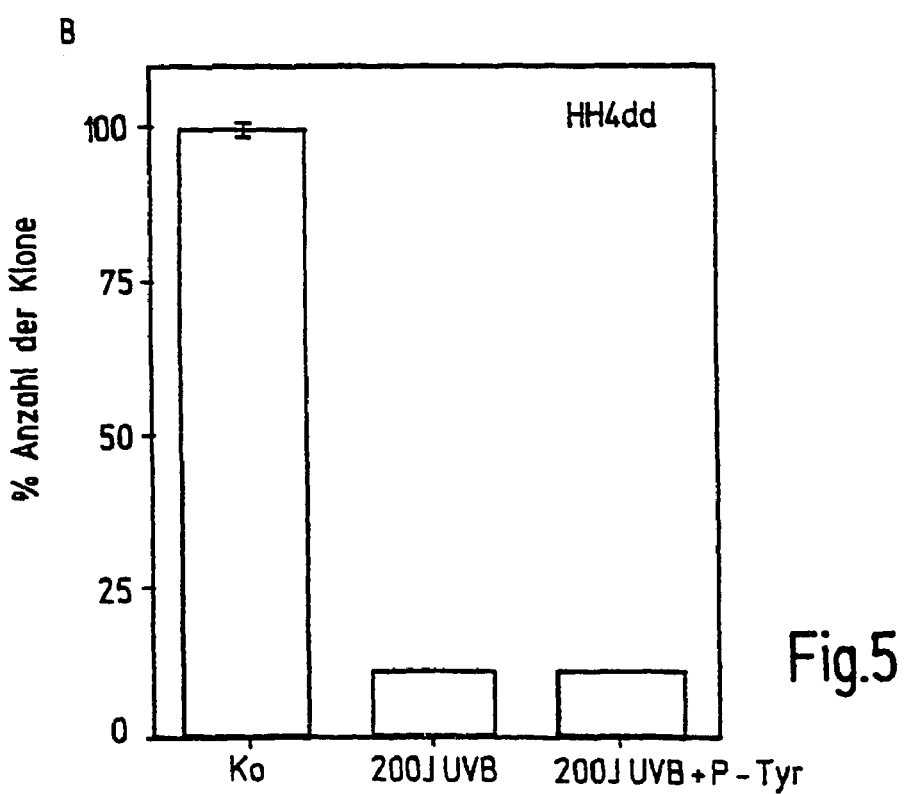

In this experiment, it is found that the clonogenic survival of UVB-irradiated normal, untransformed fibroblasts (HSF1) is increased by 37% when they have been pretreated with phosphotyrosine (see FIG. 5A, bars 2 and 3 from the left).

However, pretreatment with P-Tyr in connection with UVB irradiation had no effect on the clonogenic survival of transformed fibroblasts (HH4dd) (see FIG. 5B, bars 2 and 3 from the left).

In both cases, unirradiated cells serve as controls (Co), with the number of clones formed in this case representing 100%.

This experiment demonstrates that, in the case of non-neoplastic cells, phosphotyrosine also has cytoprotective properties in regard to nonionizing radiation. Also in this case, the cytoprotective activity is selective for normal, untransformed cells. Thus, pretreatment with P-Tyr does not have any effect on the survival of transformed cells after irradiation with UVB.

Example 8

Reaction of Fibroblasts to Cisplatin Treatment after Pretreatment with Phosphotyrosine In order to investigate the cytoprotective effect of phosphotyrosine with regard to chemical cell-damaging factors, for example cytostatic agents, normal fibroblasts (ESF1) and transformed fibroblasts (HH4dd) were pretreated for 16 hours with 10 µM P-Tyr and then, after that, incubated for one hour with 1 µg of cisplatin/ml. The cells were then washed twice with normal medium and plated 6 hours later. After that, a clonogenic assay was carried out as described under Example 3.

Figure 6:
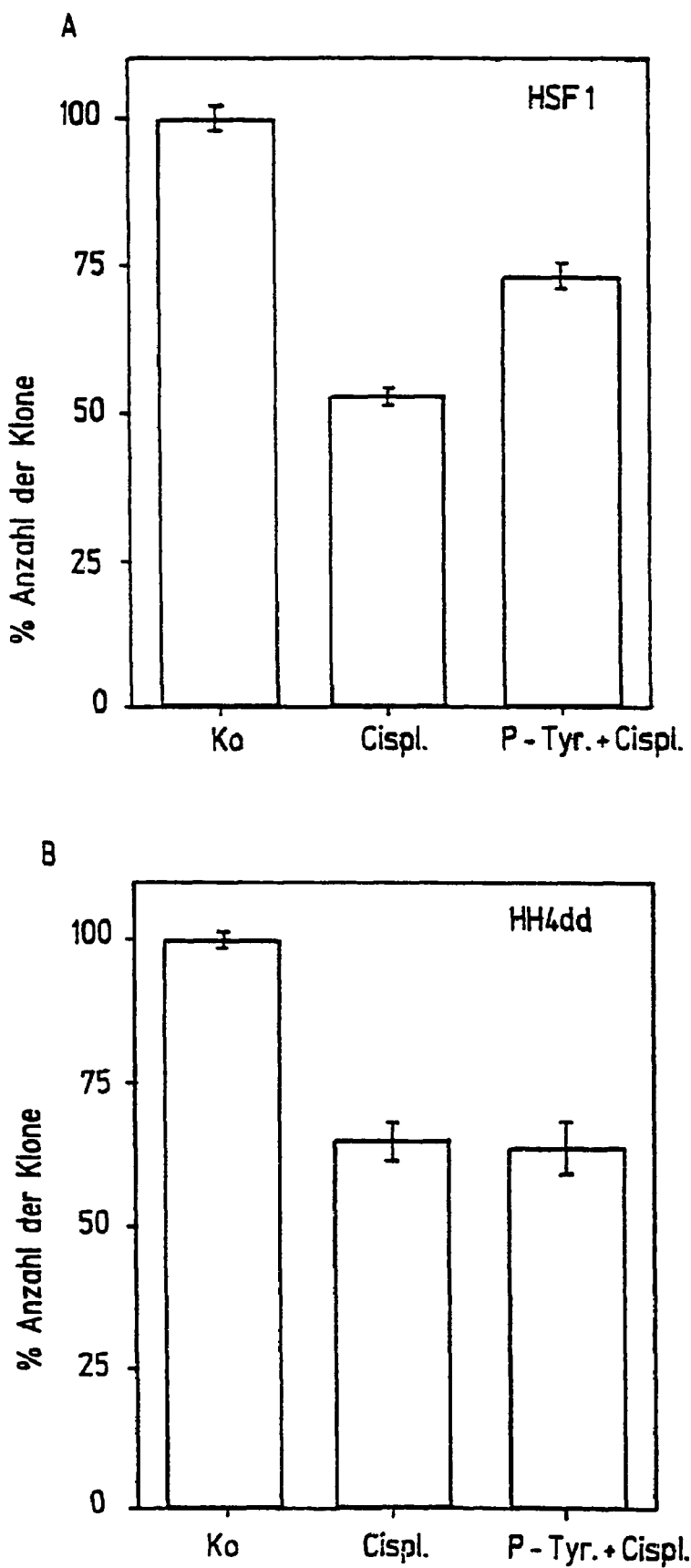
FIG. 6 shows the clonogenic survival of normal fibroblasts after treatment with cisplatin, in dependence on a pretreatment with P-Tyr, as compared with tumor cells.

FIG. 6 shows the result of such an experiment. Pretreatment of normal, untransformed fibroblasts (HSF1) with P-Tyr leads, when these fibroblasts were incubated with cisplatin, to an increase in clonogenic survival of 38.7% as compared with the clonogenic survival of transformed fibroblasts (HH4dd) which have not been pretreated (see FIG. 6A, 2nd and 3rd bars from the left).

However, a pretreatment of transformed fibroblasts (HH4dd) with P-Tyr did not lead to any increase in clonogenic survival in connection with cisplatin treatment (FIG. 6B, 2nd and 3rd bars from the left).

In controls both cases, unirradiated cells once again serve as (Co), with the number of clones formed in this case representing 100%.

Consequently, phosphotyrosine provides cytoprotection, which is selective for healthy, that is normal, cells, in regard to a cell-damaging factor of chemical nature as well.

What is claimed is:

1. A method for selectively protecting non-transformed biological cells over transformed biological cells from cell damage induced by non-ultraviolet radiation comprising:
   administering phosphotyrosine to a patient in need thereof before, during or after exposure to said non-ultraviolet radiation, wherein said non-transformed biological cells are selectively protected from cell damage as compared to said transformed biological cells.

2. The method of claim 1, wherein said radiation is ionizing radiation.

3. The method of claim 1, wherein the phosphotyrosine is administered to skin.

4. The method of claim 1, wherein said patient is a tumor patient subjected to a radiation therapy.

5. The method of claim 1, wherein said patient is a tumor patient further subjected to a chemotherapy.

6. A method of selectively protecting non-transformed biological cells over transformed biological cells during cytotoxic treatment of said transformed cells, comprising:
   administering phosphotyrosine to a patient in need thereof; and
   exposing said patient to cytotoxic, non-ultraviolet radiotherapy treatment, wherein said non-transformed biological cells are selectively protected from cell damage as compared to said transformed cells.

7. The method of claim 6, wherein said treatment further comprises chemotherapy for said transformed cells.

* * * * *